United States Patent [19]

Hoehn et al.

[11] 3,983,128

[45] Sept. 28, 1976

[54] ALCOHOL DERIVATIVES OF PYRAZOLO[3,4-b]PYRIDINES

[75] Inventors: Hans Hoehn, Tegernheim; Theodor Denzel, Nurnberg, both of Germany

[73] Assignee: E. R. Squibb & Sons, Inc., Princeton, N.J.

[22] Filed: Oct. 2, 1975

[21] Appl. No.: 618,871

Related U.S. Application Data

[62] Division of Ser. No. 423,960, Dec. 12, 1973, Pat. No. 3,928,368.

[52] U.S. Cl. .................... 260/296 H; 260/294.8 C; 260/295 F
[51] Int. Cl.² ........................................ C07D 221/00
[58] Field of Search .................. 260/296 H, 294.8 C, 260/295 F

[56] References Cited
UNITED STATES PATENTS

| | | | |
|---|---|---|---|
| 3,873,556 | 3/1975 | Benzel et al. | 260/296 H |
| 3,928,368 | 12/1975 | Hoehn et al. | 260/296 H |

FOREIGN PATENTS OR APPLICATIONS

| | | | |
|---|---|---|---|
| 2,225,433 | 12/1972 | Germany | 260/296 H |

*Primary Examiner*—John D. Randolph
*Attorney, Agent, or Firm*—Lawrence S. Levinson; Merle J. Smith; Stephen B. Davis

[57] ABSTRACT

Alcohol derivatives of pyrazolo[3,4-b]pyridines having the formula

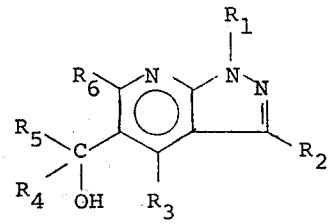

and their acid addition salts are disclosed. The novel compounds are useful as central nervous system depressants and anti-inflammatory agents. In addition, the new compounds increase the intracellular concentration of adenosine-3',5'-cyclic monophosphate.

11 Claims, No Drawings

ALCOHOL DERIVATIVES OF PYRAZOLO[3,4-b]PYRIDINES

This is a division of application Ser. No. 423,960, filed Dec. 12, 1973, now U.S. Pat. No. 3,928,368, granted Dec. 23, 1975.

BACKGROUND OF THE INVENTION

The prior art teaches the use of hydrazines, hydrazides and hydrazones of pyrazolo[3,4-b]pyridine-5-carboxylic acid and esters as central nervous system depressants as note Hoehn et al. U.S. Pat. No. 3,761,487. Surprisingly, it has been discovered that compounds having an alcohol substituent at the 5-position are also useful.

SUMMARY OF THE INVENTION

This invention relates to new 5-alcohol derivatives of pyrazolo[3,4-b]pyridines and the acid addition salts of these compounds as well as processes for producing them. These new compounds have the formula (I)

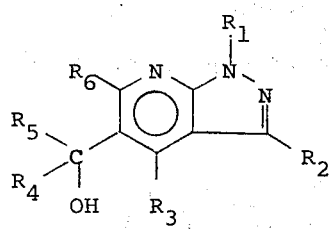

The symbols have the following meanings in formula I and throughout the specification:

$R_1$ is hydrogen, lower alkyl, phenyl, phenyl-lower alkyl, or cycloalkyl.

$R_2$ is hydrogen, lower alkyl, or phenyl.

$R_3$ is hydrogen, hydroxy, lower alkoxy, phenoxy, phenyl-lower alkoxy, halogen, or a basic nitrogen group

represents an acyclic amino moiety wherein $R_7$ and $R_8$ can each independently be hydrogen, lower alkyl, lower alkenyl, cycloalkyl,

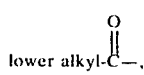

di-lower alkylamino-lower alkyl, phenyl, phenyl-lower alkyl,

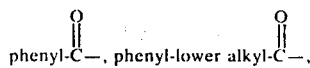

lower alkyl-sulfonyl, phenyl-sulfonyl, or substituted phenyl, phenyl-lower alkyl,

phenyl-sulfonyl.

$R_4$ and $R_5$ are each independently selected from hydrogen, lower alkyl, phenyl, substituted phenyl, phenyl-lower alkyl and cycloalkyl.

$R_6$ is hydrogen, lower alkyl, or phenyl.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, etc. The lower alkoxy groups include such lower alkyl groups bounded to an oxygen, e.g., methoxy, ethoxy, propoxy, etc. The lower alkenyl group includes compounds corresponding to the lower alkyls having one double bond, e.g., vinyl, allyl, etc.

The

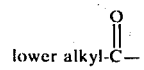

include the acyl radicals of the lower fatty acids of up to 8 carbon atoms, e.g., acetyl, propionyl, butyryl, isobutyryl and the like.

The cycloalkyl groups referred to throughout the specification include the 3 to 7 carbon atom alicyclic groups, e.g., cyclopropyl, cyclobutyl, cyclopentyl, cyclohexyl and cyclohepty. The 5 and 6-membered rings are preferred.

The substituted phenyl groups referred to throughout the specification include one or two simple substituents, i.e., lower alkyl, halogen (F, Cl, Br or I, preferably Cl or Br), trifluoromethyl, amino, or carboxy.

Preferred embodiments of this invention are as follows: $R_1$ is hydrogen, lower alkyl of 1 to 4 carbons, phenyl, benzyl, phenethyl, or cycloalkyl of 5 to 6 carbons.

$R_2$ is hydrogen, lower alkyl of 1 to 4 carbons, or phenyl.

$R_3$ is hydrogen, hydroxy, lower alkoxy of 1 to 4 carbons, phenoxy, benzyloxy, halogen, or a basic moiety,

with $R_7$ and $R_8$ independently selected from hydrogen, lower alkyl of 1 to 4 carbons, lower alkenyl of 2 to 4 carbons, cycloalkyl of 5 to 6 carbons,

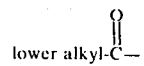

where lower alkyl is of 1 to 4 carbons, di-lower alkylamino-lower alkyl where each lower alkyl is of 1 to 4 carbons, phenyl, benzyl, phenethyl, benzoyl,

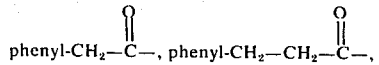

phenyl-sulfonyl, lower alkyl-sulfonyl of 1 to 4 carbons, or substituted phenyl, benzyl, phenethyl, benzoyl,

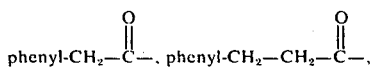

and phenyl-sulfonyl.

$R_4$ and $R_5$ are each independently selected from hydrogen, lower alkyl of 1 to 4 carbons, phenyl, substituted phenyl, benzyl, phenethyl and cycloalkyl of 5 to 6 carbons.

$R_6$ is hydrogen, lower alkyl of 1 to 4 carbons, or phenyl.

The most preferred embodiments are:

$R_1$ is hydrogen or lower alkyl of 1 to 4 carbons, especially hydrogen or ethyl.

$R_2$ is hydrogen or lower alkyl of 1 to 4 carbons, especially hydrogen or methyl.

$R_3$ is hydrogen, lower alkoxy of 1 to 4 carbons or halogen, especially hydrogen, ethoxy or Cl, or a basic moiety wherein $R_7$ and $R_8$ are independently selected from hydrogen and lower alkyl of 1 to 4 carbons, especially hydrogen or butyl.

$R_4$ and $R_5$ are independently selected from hydrogen, lower alkyl of 1 to 4 carbons, or phenyl, especially hydrogen, ethyl, butyl, or phenyl.

$R_6$ is hydrogen or lower alkyl of 1 to 4 carbons, especially hydrogen or methyl.

DETAILED DESCRIPTION OF THE INVENTION

The new compounds of formula I may be produced by several methods.

According to one procedure, when $R_1$ is other than hydrogen, a product of formula I may be produced from compounds of the formula (II)

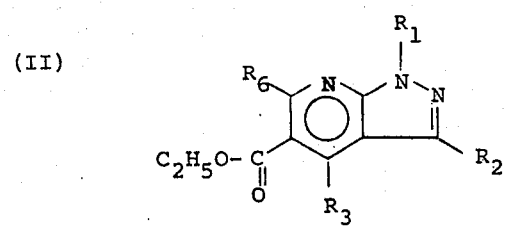

or from compounds of the formula (III)

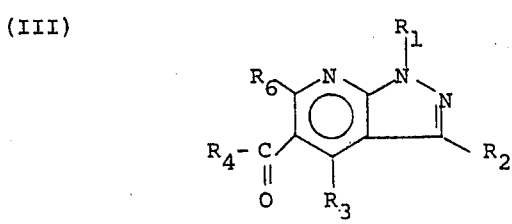

The compounds of formula II and III are formed by the following series of reactions. The symbols in the structural formulas have the same meaning as previously described.

A 5-aminopyrazole of the formula (IV)

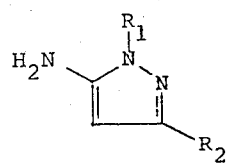

[prepared according to the procedure described in Z. f. Chemie 10, 386–388 (1970)] is made to react either with an alkoxymethylene malonic acid ester or an alkoxymethylene acyl acetic acid ester of the formula (V)

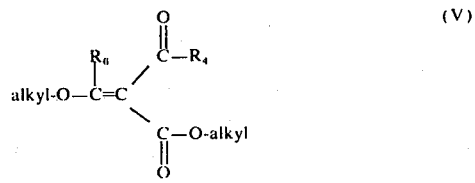

in which $R_4$ represents an ethoxy group or a substituent previously described, by heating at a temperature of about 120°C.

The resulting compound of the formula (VI)

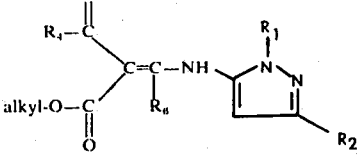

undergoes cyclization in an inert organic solvent such as diphenylether at about 230° to 260°C., while distilling off the alcohol formed, producing compounds of the formula (VII)

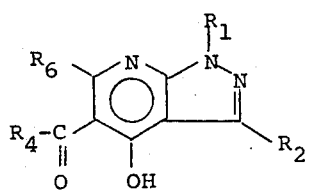

Alternatively, instead of allowing the compound of formula VI to undergo cyclization as described above, this product can be cyclized by treatment with phosphorous oxychloride producing the chlorine product of formula (VIII)

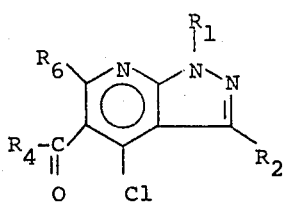

The resulting compounds of formula VII and VIII in turn can be converted to derivatives of formula II and III according to known reaction routes.

The product of formula I is then prepared by reduction of either compounds of formulas II and III or of formulas VII and VIII by means of reduction agents, e.g.: LiAlH$_4$ and the like.

Alternatively, instead of allowing the pyrazolopyridines of formulas II, III, VII and VIII to undergo reduction in an inert organic solvent at room or elevated temperatures as described above, these compounds undergo Grignard reaction by alkyl (aryl) magnesium halogenids producing alcohols of the formula I.

There is no limit concerning the introduction of the substituent in position 4 of the molecule. Variations at this position can take place before or after the reduction step.

According to a modification of the foregoing procedure a product of formula I wherein R$_1$ is hydrogen may be produced. By this modification a 5-aminopyrazole of formula II, wherein R$_1$ is an arylmethyl group or a heteromethyl group is used. This starting material has the formula

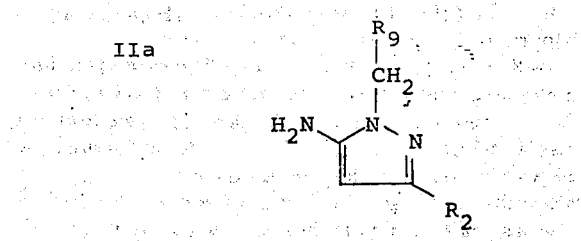

wherein R$_9$ is an aromatic or heterocyclic nucleus such as furyl, pyridyl, pyrimidyl or the like.

This material is processed as described above through the reaction with the ester of formula V to obtain a compound of formula VII with a hydroxy group in 4-position. Alkylating leads to a compound of formula

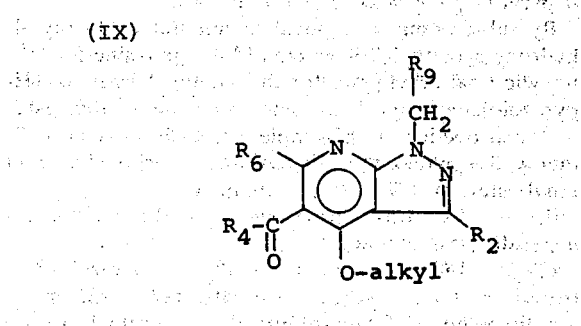

At this point, the compound of formula IX having in the 1-position the R$_9$—CH$_2$— substituent is oxidized with an oxidizing agent such as selenium dioxide in a high boiling solvent such as diethylene glycol dimethyl ether at about 160° yielding the compound of the formula

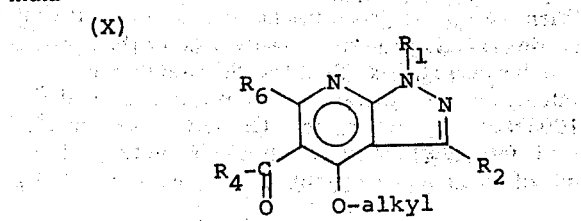

wherein R$_1$ is hydrogen. This type of compound can be converted to derivatives carrying a substituent in the 4-position of the meaning of R$_3$ instead of O-alkyl.

The bases of formula I form acid addition pharmaceutically acceptable salts by reaction with equivalent amounts of the common inorganic and organic acids. Examples of such acid addition salts are the hydrohalides (especially the hydrochloride), sulfate, nitrate, phosphate, oxalate, tartrate, malate, citrate, acetate, ascorbate, succinate, benzenesulfonate, toluenesulfonate, cyclohexanesulfamate, etc. The acid-addition salts frequently provide a convenient means for isolating the product, e.g., by forming and precipitating the salt in an appropriate menstruum in which the salt is insoluble, then after separation of the salt, neutralizing with a base such as barium hydroxide or sodium hydroxide, to obtain the free base of formula I. Other salts may then be formed from the free base by reaction with an equivalent of acid.

The new compounds of this invention and their acid addition salts have anti-inflammatory properties and are useful as anti-inflammatory agents, for example, to reduce local inflammatory conditions such as those of an edematous nature or resulting from proliferation of connective tissue in various mammalian species such as rats, dogs and the like when given orally in dosages of about 5 to 50 mg/kg/day, preferably 5 to 25 mg/kg/day, in single or 2 to 4 divided doses, as indicated by the carageenan edema assay in rats. The active substance may be utilized in compositions such as tablets, capsules, solutions or suspensions containing up to about 300 mg. per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, salve or cream may also be used.

The new compounds of this invention and their acid addition salts also have central nervous system depressant activity and can be used as tranquilizers or ataractic agents for the relief of anxiety and tension states, for example, in mice, cats, rats, dogs and other mammalian species, in the same manner as chlordiazepoxide. For this purpose a compound or mixture of compounds of formula I is administered orally or parenterally in a conventional dosage form such as tablet, capsule, injectable or the like. A single dose, or preferably 2 to 4 divided daily doses, provided on a basis of about 1 to 50 mg. per kilogram per day, preferably about 2 to 15 mg. per kilogram per day, is appropriate. These may be conventionally formulated in an oral or parenteral dosage form by compounding about 10 to 250 mg. per unit of dosage with conventional vehicle, excipient, binder, preservative, stabilizer, flavor or the like as called for by accepted pharmaceutical practice.

The new compounds and their acid addition salts also increase the intracellular concentration of adenosine-3'',5'-cyclic monophosphate, and thus by the administration of about 1 to 100 mg/kg/day, preferably about 10 to 50 mg/kg, in single or two to four divided doses in conventional oral or parenteral dosage forms such as those described above may be used to alleviate the symptoms of asthma.

The following examples are illustrative of the invention. All temperatures are expressed on the centigrade scale.

EXAMPLE 1

4-Chloro-1-ethyl-1H-pyrazolo[3,4-b]pyridine-5-methanol a. [[(1-Ethyl-5-pyrazolyl)amino]methylene]malonic acid diethyl ester 245 g. 1-Ethyl-5-aminopyrazole (2.2 mol.) and 476 g. ethoxymethylene malonic acid diethyl ester (2.2 mol.) are heated to 120° (bath temperature) for 2 hours with stirring. The ethanol formed by this reaction is removed by means of a water aspirator. Vacuum distillation (b.p. $_{0.1}$ 154°–160°) yields 520 g. (84%) of a quick crystallizing oil of [[(1-ethyl-5-pyrazolyl)amino]methylene]malonic acid diethyl ester, m.p. 50°–53°.

The compound is recrystallized from N-hexane, m.p. 55°–57°.

The hydrochloride salt is formed by treating the above product with dilute ethanolic hydrogen chloride solution.

b. 1-Ethyl-4-hydroxy-1H-pyrazolo[3,4-b]pyridine-5-carboxylic acid and ethyl ester 253 g. [[(1-Ethyl-5-pyrazolyl)amino]methylene]malonic acid diethyl ester (0.09 mol.) are dissolved in 770 g. of diphenyl ether. The reaction mixture is heated to 235°–250° (bath temperature) and allowed to react at this temperature for 1–2 hours while the resulting ethanol is continuously distilled off. The last amount of alcohol is removed by means of a water aspirator. The diphenyl ether is separated by distillation with a fractionating column in vacuo. The 1-ethyl-4-hydroxy-1H-pyrazolo[3,4-b]pyridine-5-carboxylic acid ethyl ester is obtained at b.p. $_{0.05}$ 115°–120°, yield 195 g. (92%), m.p. 85°–87°. The compound is recrystallized from ligroin (90°–100°), m.p. 87°–89°. Hydrolysis of this product with aqueous sodium hydroxide yields 1-ethyl-4-hydroxy-1H-pyrazolo[3,4-b]pyridine-5-carboxylic acid, m.p. 201°–202°.

c. 4-Chloro-1-ethyl-1H-pyrazolo[3,4-b]pyridine-5-carboxylic acid ethyl ester

A mixture of 23.5 g. 1-ethyl-4-hydroxy-1H-pyrazolo[3,4-b]pyridine-5-carboxylic acid ethyl ester (0.1 mol.) and 150 ml. of phosphorous oxychloride is refluxed for 4 hours. Subsequently, the excess phosphorous oxychloride is removed by means of vacuum distillation. As soon as the phosphorous oxychloride has been removed, the oily residue solidifies on cooling. It is treated with water and filtered under suction (24.5 g., m.p. 55°–60°). The 4-chloro compound is recrystallized from N-hexane (22.5 g. (87%), m.p. 62°).

d. 4-Chloro-1-ethyl-1H-pyrazolo[3,4-b]pyridine-5-methanol 10.02 g. of 4-Chloro-1-ethyl-1H-pyrazolo[3,4-b]pyridine-5-carboxylic acid ethyl ester (0.04 mol.) are dissolved in 100 ml. of anhydrous tetrahydrofuran. Nitrogen is passed through the flask and while stirring and cooling with tap water, 1.14 g. of lithium aluminium hydride is added a bit at a time in order to keep the reaction temperature at about 25°C. Stirring is continued for an additional two hours at room temperature. The reaction mixture is allowed to stand over night. Then 3 N-hydrochloric acid (60 ml) is added and the mixture is evaporated in vacuo. The residue is dissolved in water, neutralized with aqueous sodium hydroxide (10%) to pH 7 and extracted several times with ether. The combined ethereal extracts are dried with sodium sulfate, evaporated and the residual oil (6.7 g. (79%)) is distilled in vacuo, b.p. $_{0.4\,mm}$ 137°–140°, providing a quickly crystallizing oil. The compound is recrystallized from hexane, to yield the 4-chloro-1-ethyl-1H-pyrazolo[3,4-b]pyridine-5-methanol, m.p. 56°.

EXAMPLE 2

4-Chloro-1-ethyl-3-methyl-1H-pyrazolo[3,4-b]pyridine-5-methanol a. [[(1-Ethyl-3-methyl-5-pyrazolyl)amino]methylene]malonic acid diethyl ester 12.5 g. of 1-Ethyl-3-methyl-5-aminopyrazole (0.1 mol.) and 21.6 g. of ethoxymethylene malonic acid diethyl ester (0.1 mol.) are heated to 120° (bath temperature) for 2 hours with stirring. The ethanol formed by this reaction is removed by means of a water aspirator. Vacuum distillation (b.p. $_{0.05}$ 152°–153°) yields 24.0 g. (81.5%) of a quickly crystallizing oil, [[(1-ethyl-3-methyl-5-pyrazolyl)amino]methylene]malonic acid diethyl ester, m.p. 60°–67°. The product, recrystallized from ligroin (90°–100°), melts at 69°–70°.

b. 1-Ethyl-4-hydroxy-3-methyl-1H-pyrazolo[3,4-b]pyridine-5-carboxylic acid ethyl ester 14.8 g. of [[(1-Ethyl-3-methyl-5-pyrazolyl)amino]methylene]malonic acid diethyl ester (0.05 mol.) are dissolved in 50 g. of diphenyl ether. The reaction mixture is heated to 235°–250° (bath temperature) and allowed to react at this temperature for 1 to 2 hours, while the resulting ethanol is continuously distilled off. The last part of the alcohol is removed by means of a water aspirator. The diphenyl ether is separated by distillation with a fractionating column in vacuo. The 1-ethyl-4-hydroxy-3-methyl-1H-pyrazolo[3,4-b]pyridine-5-carboxylic acid ethyl ester is obtained at b.p. $_{0.1-0.5}$ 125°–129°, yield 10.7 g. (86%), m.p. 91°–93°. The compound is recrystallized from ligroin (90°–100°), m.p. 93°–94°.

c. 4-Chloro-1-ethyl-3-methyl-1H-pyrazolo[3,4-b]pyridine-5-carboxylic acid ethyl ester By substituting an equivalent amount of 1-ethyl-4-hydroxy-3-methyl-1H-pyrazolo[3,4-b]pyridine-5-carboxylic acid ethyl ester for the 1-ethyl-4-hydroxy-1H-pyrazolo[3,4-b]pyridine-5-carboxylic acid ethyl ester in the procedure of Example 1c, 4-chloro-1-ethyl-3-methyl-1H-pyrazolo[3,4-b]pyridine-5-carboxylic acid ethyl ester, m.p. 78°–80°, is obtained.

d. 4-Chloro-1-ethyl-3-methyl-1H-pyrazolo[3,4-b]pyridine-5-methanol 63 g. of 4-Chloro-1-ethyl-3-methyl-1H-pyrazolo[3,4-b]pyridine-5-carboxylic acid ethyl ester (0.235 mol.) are dissolved in 360 ml. of anhydrous tetrahydrofuran. Nitrogen is passed through the flask and while stirring and cooling with tap water, 5.2 g. of lithium aluminium hydride is added a bit at a time so that the reaction temperature does not exceed 25°. Stirring is continued for 2 hours at room temperature. Without further stirring the reaction mixture is allowed to stand over night. Then 300 ml. of 3N-hydrochloric acid is added while stirring and cooling with ice-water to keep the temperature between 15° and 20°. The clear solution is evaporated to dryness in vacuo, the residue is treated with 100 ml of water and precipitated starting material (5–6 g.) is filtered off. Then the filtrate is diluted with 300 ml. of water and refrigerated over night. 32–39.3 g.

(60–74%) of 4-chloro-1-ethyl-3-methyl-1H-pyrazolo[3,4-b]pyridine-5-methanol which crystallizes is filtered and dried at 70°, m.p. 119°–21°. The compound is recrystallized from acetonitrile, m.p. 121°–122°. Acidification of the aqueous mother liquor with hydrochloric acid, evaporation in vacuo and extraction of the residue by means of boiling acetonitrile yielded up to 15 g. of the starting material in form of the hydrochloride.

EXAMPLE 3

4-Ethoxy-1-ethyl-1H-pyrazolo[3,4-b]pyridine-5-methanol a. 4-Ethoxy-1-ethyl-1H-pyrazolo[3,4-b]pyridine-5-carboxylic acid ethyl ester In a solution of 259 g. 1-ethyl-4-hydroxy-1H-pyrazolo[3,4-b]pyridine-5-carboxylic acid ethyl ester (1.1 mol.) in 1700 ml. dimethylformamide, 400 g. of well pulverized potassium carbonate and 300 g. of ethyl iodide are introduced. The reaction mixture is stirred for 7 hours at 65° and filtered under suction, while hot, to remove excess potassium carbonate. Upon standing over night, 165 g. of 4-ethoxy-1-ethyl-1H-pyrazolo[3,4-b]pyridine-5-carboxylic acid ethyl ester crystallize out of the solution, m.p. 112°–115°. After evaporation of the mother liquor, an additional 80 g. are obtained. The total yield amounts to 85% of theory. The compound is recrystallized from ligroin (90°–100°), m.p. 113°–115°.

b. 4-Ethoxy-1-ethyl-1H-pyrazolo[3,4-b]pyridine-5-methanol 115 g. of 4-Ethoxy-1-ethyl-1H-pyrazolo[3,4-b]pyridine-5-carboxylic acid ethyl ester (0.438 mol.) are dissolved in 1.7 liters of anhydrous tetrahydrofuran. Nitrogen is passed through the flask and while stirring and cooling with tap water 12.5 g. of lithium aluminium hydride is added in portions in order to prevent the temperature from exceeding 22°. The mixture is stirred at room temperature for 1 hour and then at reflux temperature for 2 hours. While stirring and cooling with ice-water, 600 ml. of hydrochloric acid (3 N) is added drop by drop and the reaction mixture is allowed to stand over night. Then the clear solution is evaporated to dryness in vacuo and the residue is treated with 1.6 liters of hot absolute alcohol dissolving mainly AlCl₃ and LiCl but leaving 45.3 g. of 4-ethoxy-1-ethyl-1H-pyrazolo[3,4-b]pyridine-5-methanol hydrochloride (m.p. 170°–171° dec.). An additional amount of 14.1 g. of hydrochloride precipitates from the alcoholic solution. Yield 59.4 g. (52.5%). Neutralization of the hydrochloride by means of aqueous sodium hydroxide and extracting with chloroform provides the free compound, m.p. 100°–102°.

EXAMPLE 4

4-Butylamino-1-ethyl-1H-pyrazolo[3,4-b]pyridine-5-methanol a. 4-Butylamino-1-ethyl-1H-pyrazolo[3,4-b]pyridine-5-carboxylic acid ethyl ester To a solution of 50.8 g. of 4-chloro-1-ethyl-1H-pyrazolo[3,4-b]pyridine-5-carboxylic acid ethyl ester (0.2 mol.) in 200 ml. of benzene, 29.2 g. of n-butylamine (0.4 mol.) are added. The mixture is kept at 50° for 5 hours. Then the separated butylamine hydrochloride is filtered under suction and the filtrate is evaporated in vacuo to dryness. The residual 4-butylamino-1-ethyl-1H-pyrazolo[3,4-b]pyridine-5-carboxylic acid ethyl ester is recrystallized from hexane, m.p. 82°–83°, yield 53 g. (91.5%).

b. 4-Butylamino-1-ethyl-1H-pyrazolo[3,4-b]pyridine-5-methanol and hydrochloride 46 g. of 4-Butylamino-1-ethyl-1H-pyrazolo[3,4-b]pyridine-5-carboxylic acid ethyl ester (0.159 mol.) are dissolved in 400 ml. of anhydrous tetrahydrofuran. Nitrogen is passed through the flask and while stirring and cooling with tap water, 4.55 g. of lithium aluminium hydride is added in portions so that the reaction temperature does not exceed 25°. Stirring is continued first at room temperature for 3 hours, then at 50° for one hour and subsequently the mixture is allowed to stand over night without stirring. 320 ml. of Hydrochloric acid (3 N) is added a drop at a time to the mixture with stirring while cooling with ice water. The clear solution is evaporated to dryness in vacuo and the residue is dissolved in a small quantity of water. By cooling the solution in the refrigerator, 21.6 g. of the hydrochloride of 4-butylamino-1-ethyl-1H-pyrazolo[3,4-b]pyridine-5-methanol is obtained, m.p. 164°–165°. The aqueous filtrate is alkalized with diluted aqueous sodium hydroxide and extracted a few times with ether. Evaporation of the ether yields 20.6 g. of the free compound. Recrystallization from hexane, m.p. 86°–87°.

EXAMPLE 5

4-Butylamino-1-ethyl-1H-pyrazolo[3,4-b]pyridine-5-methanol 51 g. of 4-Chloro-1-ethyl-1H-pyrazolo[3,4-b]pyridine-5-methanol (0.24 mol.) and 300 ml. of n-butylamine are heated at 100° in an autoclave for seven hours. After cooling, the surplus butylamine is removed by distillation in vacuo and the residue is treated with a total amount of 200 ml. of ether. The etheral solution is evaporated, yielding 51.9 g (87%) of the alcohol, m.p. 60°–72°. Recrystallization with hexane provides the pure 4-butylamino-1-ethyl-1H-pyrazolo[3,4-b]pyridine-5-methanol, m.p. 85°–86°.

EXAMPLE 6

4-Butylamino-1-ethyl-3-methyl-1H-pyrazolo[3,4-b]pyridine-5-methanol

By treating the 4-chloro-1-ethyl-3-methyl-1H-pyrazolo[3,4-b]pyridine-5-methanol of Example 2 with butylamino as in Example 5, 4-btuylamino-1-ethyl-3-methyl-1H-pyrazolo[3,4-b]pyridine-5-methanol is obtained. Yield 88%, m.p. 80°–81°, hydrochloride m.p. 189°–90°.

EXAMPLE 7

4-Ethoxy-1-ethyl-3-methyl-1H-pyrazolo[3,4-b]pyridine-5-methanol

By treating the 4-ethoxy-1-ethyl-3-methyl-1H-pyrazolo[3,4-b]pyridine-5-carboxylic acid ethyl ester (prepared by combining the procedures of Examples 2b and 3a, m.p. 93°–94°) with lithium aluminium hydride as in Example 3b, 4-ethoxy-1-ethyl-3-methyl-1H-pyrazolo[3,4-b]pyridine-5-methanol is obtained. Yield 82%, m.p. 85°–86°.

EXAMPLE 8

1-Ethyl-3-methyl-1H-pyrazolo[3,4-b]pyridine-5-methanol

By treating 1-ethyl-3-methyl-1H-pyrazolo[3,4-b]pyridine-5-carboxylic acid ethyl ester (prepared by catalytical reduction of 4-chloro-1-ethyl-3-methyl-1H-pyrazolo[3,4-b]pyridine-5-carboxylic acid ethyl ester (Example 2c) by means of palladium on charcoal, m.p. 54°–56°) with lithium aluminium hydride as in Example 1d or 3b, 1-ethyl-3-methyl-1H-pyrazolo[3,4-b]pyridine-5-methanol hydrochloride is obtained. Yield 78%, m.p. 168°–69°.

EXAMPLE 9

4-Butylamino-1-ethyl-1H-pyrazolo[3,4-b]pyridine-5-diethyl carbinol 10 g. of 4-Butylamino-1-ethyl-1H-pyrazolo[3,4-b]pyridine-5-carboxylic acid ethyl ester prepared according to Example 4a are dissolved in 100 ml. of dry ether. 51.8 ml. of an Ethyl magnesium iodide Grignard solution (prepared from 12.6 g. of magnesium and 8 g. of ethyl iodide in 150 ml. of anhydrous ether) are added dropwise with stirring under a nitrogen atmosphere. The solution is refluxed for 24 hours. The mixture is decomposed with 10 ml. of water and acidified with acetic acid. The organic layer is separated and the aqueous phase extracted twice with 20 ml. portions of ether. The combined organic layers are dried with sodium sulfate, filtered and evaporated to dryness. Recrystallization of the residue yields 8 g. of 4-butylamino-1-ethyl-1H-pyrazolo[3,4-b]pyridine-5-diethyl carbinol (76%), m.p. 112°–115°.

EXAMPLE 10

4-Ethoxy-1-ethyl-1H-pyrazolo[3,4-b]pyridine-5-diethyl carbinol 10 g. of 4-Ethoxy-1-ethyl-1H-pyrazolo[3,4-b]pyridine-5-carboxylic acid ethyl ester prepared according to Examples 3a are dissolved in 80 ml. of dry ether. 57.5 ml. of an Ethyl magnesium iodide Grignard solution (prepared from 12.6 g. of magnesium and 8 g. of ethyl iodide in 150 ml. of anhydrous ether) are added dropwise with continuous stirring under and inert gas atmosphere. The resulting solution is kept at reflux temperature for 20 hours. After this time, the mixture is decomposed with 10 ml. of water and acidified with acetic acid. The organic layer is separated and the aqueous phase is extracted twice with 20 ml. portions of ether. The combined ether layers are dried over sodium sulfate, filtered and evporated to dryness. Recrystallization from petrol ether yields 6 g. of the carbinol (55%), m.p. 61°–63°.

EXAMPLE 11

4-Amino-1H-pyrazolo[3,4-b]pyridine-5-phenyl carbinol a. [[[1-(2-furyl)methyl-5-pyrazolyl]amino]methylene]benzoyl acetic acid ethyl ester 163 g. of 1-(2-furyl)methyl-5-aminopyrazole (1 mol.) and 248 g. of ethoxymethylene benzoyl acetic acid ethyl ester (1 mol.) are heated at 130° until no more alcohol distils off (approximately 1 hour). The oily residue crystallizes and yields on cooling and recrystallization from hexane 310 g. of [[[1-(2-furyl)methyl-5-pyrazolyl]-amino]methylene]benzoyl acetic acid ethyl ester (85%), m.p. 75°–77°.

b. 5-Benzoyl-4-hydroxy-1-(2-furyl)methyl-1H-pyrazolo[3,4-b]pyridine 36.5 g. of [[[1-(2-furyl)methyl-5-pyrazolyl]amino]-methylene]benzoyl acetic acid ethyl ester are dissolved in 50 ml. of diphenyl ether and refluxed at 260° for 30 minutes. Distillation of the solvent yields a dark oil, which crystallizes on addition of methanol. Recrystallization yields 20 g. of 5-benzoyl-4-hydroxy-1-(2-furyl)-methyl-1H-pyrazolo[3,4-b]pyridine (61%), m.p. 102°.

c. 5-Benzoyl-4-ethoxy-1-(2-furyl)methyl-1H-pyrazolo[3,4-b]pyridine 3.3 g. of 5-Benzoyl-4-hydroxy-1-(2-furyl)methyl-1H-pyrazolo[3,4-b]pyridine (0.01 mol.) are dissolved in 20 ml. of dimethylformamide. 2.8 g. of potassium carbonate and 3.1 g. of ethyl iodide are added and the mixture is warmed for 12 hours at 60°. Excess potassium carbonate is filtered off and water is added. 5-Benzoyl-4-ethoxy-1-(2-furyl)methyl-1H-pyrazolo[3,4-b]pyridine precipitates and is recrystallized from hexane, yield 3 g. (86%), m.p. 70°.

d. 5-Benzoyl-4-ethoxy-1H-pyrazolo[3,4-b]pyridine 1.7 g. of 5-Benzoyl-4-ethoxy-1-(2-furyl)methyl-1H-pyrazolo[3,4-b]pyridine (0.005 mol.) are dissolved in 5 ml. of diethyleneglycol dimethyl ether, 1.1 g. of selenium dioxide are added and the mixture is heated with stirring at 160°. After the addition of 1 drop of water, the temperature is maintained for 1 hour. The mixture is filtered hot and 5-benzoyl-4-ethoxy-1H-pyrazolo[3,4-b]pyridine precipitates on cooling. Recrystallization from butanol yields 1 g. (77%). m.p. 195°–197°.

e. 4-Amino-5-benzoyl-1H-pyrazolo[3,4-b]pyridine 2.6 g. of 5-Benzoyl-4-ethoxy-1H-pyrazolo[3,4-b]pyridine (0.01 mol.) are dissolved in 50 ml. of n-butyl alcohol, 10 ml. of aqueous ammonia (32%) are added and the mixture is heated for 10 hours in an autoclave at 160°. After this period, the excess solvent is removed in vacuo and the residue is recrystallized from n-butyl alcohol, yielding 2.1 g. of 4-amino-5-benzoyl-1H-pyrazolo[3,4-b]pyridine (83%), m.p. 282°–283°.

f. 4-Amino-1H-pyrazolo[3,4-b]pyridine-5-phenyl carbinol 1.5 g. of 4-Amino-5-benzoyl-1H-pyrazolo[3,4-b]pyridine are suspended in 30 ml. of dry dioxane. 0.4 g. of Lithium alanate are added and the mixture is refluxed for 6 hours. After this time, the solution is cooled, 0.5 ml. of water and 0.5 ml. of a 15% sodium hydroxide solution are added drop by drop. The reaction mixture is filtered, evaporated to dryness and the residue recrystallized from methanol/water to give the 4-amino-1H-pyrazolo[3,4-b]pyridine-5-phenyl carbinol, m.p. 216°–218°.

EXAMPLE 12

4-Butylamino-1-ethyl-1H-pyrazolo[3,4-b]pyridine-5-diphenyl carbinol

By reacting 4-butylamino-1-ethyl-1H-pyrazolo[3,4-b]pyridine-5-carboxylic acid ethyl ester of Example 4a with phenyl magnesium iodide according to the procedure of Example 9, 4-butylamino-1-ethyl-1H-pyrazolo[3,4-b]pyridine-5-diphenyl carbinol is obtained, m.p. 129°–134°.

EXAMPLE 13

4-Butylamino-1-ethyl-1H-pyrazolo[3,4-b]pyridine-5-dibutyl carbinol

By reacting 4-ethoxy-1-ethyl-1H-pyrazolo[3,4-b]pyridine-5-carboxylic acid ethyl ester of Example 3a with butyl magnesium iodide according to the procedure of Example 9, 4-butylamino-1-ethyl-1H- pyrazolo[3,4]pyridine-5-dibutyl carbinol is obtained, m.p. 94°–96°.

EXAMPLES 14–17

Following the procedure of Example 2 but employing the substituted aminopyrazole of column I one obtains the product of column II.

| Column I | Column II |
|---|---|
| 1-ethyl-3-phenyl-5-aminopyrazole | 4-chloro-1-ethyl-3-phenyl-1H-pyrazolo[3,4-b]pyridine-5-methanol |
| 1,3-diethyl-5-aminopyrazole | 4-chloro-1,3-diethyl-1H-pyrazolo[3,4-b]pyridine-5-methanol |
| 1-ethyl-3-isopropyl-5-aminopyrazole | 4-chloro-1-ethyl-3-isopropyl-1H-pyrazolo[3,4-b]pyridine-5-methanol |
| 1-ethyl-3-isobutyl-5-aminopyrazole | 4-chloro-1-ethyl-3-isobutyl-1H-pyrazolo[3,4-b]pyridine-5-methanol |

EXAMPLES 18–25

Following the procedure of Example 1 but employing the substituted -5-aminopyrazoles of column I the following products of column II are obtained:

| Column I substituted-5-aminopyrazole | Column II product |
|---|---|
| 1-methyl-5-aminopyrazole | 4-chloro-1-methyl-1H-pyrazolo[3,4-b]pyridine-5-methanol |
| 1-isobutyl-5-aminopyrazole | 4-chloro-1-isobutyl-1H-pyrazolo[3,4-b]pyridine-5-methanol |
| 1-isopropyl-5-aminopyrazole | 4-chloro-1-isopropyl-1H-pyrazolo[3,4-b]pyridine-5-methanol |
| 1-phenyl-5-aminopyrazole | 4-chloro-1-phenyl-1H-pyrazolo[3,4-b]pyridine-5-methanol |
| 1-benzyl-5-aminopyrazole | 4-chloro-1-benzyl-1H-pyrazolo[3,4-b]pyridine-5-methanol |
| 1-phenethyl-5-aminopyrazole | 4-chloro-1-phenethyl-1H-pyrazolo[3,4-b]pyridine-5-methanol |
| 1-cyclopentyl-5-aminopyrazole | 4-chloro-1-cyclopentyl-1H-pyrazolo[3,4-b]pyridine-5-methanol |
| 1-cyclohexyl-5-aminopyrazole | 4-chloro-1-cyclohexyl-1H-pyrazolo[3,4-b]pyridine-5-methanol |

EXAMPLE 26

Following the procedure of Example 9 but employing appropriate Grignard solutions the following compounds of Formula I are obtained:

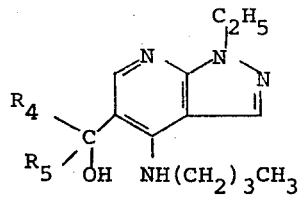

| $R_4$ | $R_5$ |
|---|---|
|  |  |
| CF$_3$-Ph- | CF$_3$-Ph- |
| CH$_3$-Ph- | CH$_3$-Ph- |
| NH$_2$-Ph- | NH$_2$-Ph- |
| HOOC-Ph- | HOOC-Ph- |
| 3,4-diCl-Ph- | 3,4-diCl-Ph- |
| 3,5-diCH$_3$-Ph- | 3,5-diCH$_3$-Ph- |
| Ph-CH$_2$- | Ph-CH$_2$- |
| Ph-CH$_2$-CH$_2$- | Ph-CH$_2$-CH$_2$- |
| cyclopentyl | cyclopentyl |
| cyclohexyl | cyclohexyl |
| i-C$_3$H$_7$ | i-C$_3$H$_7$ |
| CH$_3$ | CH$_3$ |

EXAMPLE 27

Following the procedure of Example 4 but substituting for the n-butylamine the appropriate amines the following compounds are obtained:

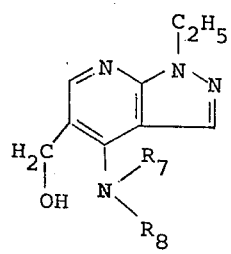

| $R_7$ | $R_8$ |
|---|---|
| H | cyclopentyl |
| H | cyclohexyl |
| H | -C₆H₅ (phenyl) |
| H | -CH₂-C₆H₅ |
| H | -CH₂-CH₂-C₆H₅ |
| H | -C₆H₄-Cl |
| H | -C₆H₄-CH₃ |
| H | -C₆H₄-NH₂ |
| H | -C₆H₄-CF₃ |
| H | -C₆H₄-COOH |
| H | -C₆H₃(Cl)₂ (2,4-dichlorophenyl) |
| H | -C₆H₃(CH₃)₂ (3,5-dimethylphenyl) |
| H | -CH₂-C₆H₄-CH₃ |
| H | -CH₂-CH₂-C₆H₄-Br |
| H | -CH₂-C₆H₄-CF₃ |
| H | -CH₂-C₆H₄-NH₂ |
| H | -CH₂-C₆H₃(Cl)₂ (2,4-dichlorobenzyl) |
| H | -C(O)-C₆H₅ |
| H | -C(O)-CH₂-C₆H₅ |
| H | -C(O)-CH₂-CH₂-C₆H₅ |
| H | -C(O)-C₆H₄-CH₃ |
| H | -C(O)-C₆H₄-Cl |
| H | -C(O)-C₆H₄-NH₂ |
| H | -C(O)-C₆H₄-Br |
| H | -C(O)-CH₂-C₆H₄-Cl |
| H | -C(O)-CH₂-CH₂-C₆H₄-CH₃ |
| H | -C(O)-CH₂-C₆H₄-CF₃ |
| H | -C(O)-CH₂-C₆H₄-NH₂ |
| H | -C(O)-CH₂-C₆H₃(CH₃)₂ (3,5-dimethyl) |
| H | -C(O)-CH₂-C₆H₃(Cl)₂ (2,4-dichloro) |
| H | -CH=CH₂ |
| H | -CH₂-CH=CH₂ |
| H | -CH₂-CH₂-CH=CH₂ |
| H | -CH₂-CH₂-CH₂-N(CH₃)₂ |

-continued

| $R_7$ | $R_8$ |
|---|---|
| H | $-CH_2-CH_2-CH_2-N\begin{matrix}C_2H_5\\C_2H_5\end{matrix}$ |
| H | $CH_3$ |
| H | $C_2H_5$ |
| H | $i-C_3H_7$ |
| H | $-\underset{O}{\overset{O}{\underset{\|}{S}}}-CH_3$ |
| H | $-\underset{O}{\overset{O}{\underset{\|}{S}}}-C_2H_5$ |
| H | $-\underset{O}{\overset{O}{\underset{\|}{S}}}-(CH_2)_2CH_3$ |
| H | $-\underset{O}{\overset{O}{\underset{\|}{S}}}-(CH_2)_3CH_3$ |
| H | $-\underset{O}{\overset{O}{\underset{\|}{S}}}-\text{C}_6H_5$ |
| H | $-\underset{O}{\overset{O}{\underset{\|}{S}}}-\text{C}_6H_4-CH_3$ |
| H | $-\underset{O}{\overset{O}{\underset{\|}{S}}}-\text{C}_6H_4-Cl$ |
| H | $-\underset{O}{\overset{O}{\underset{\|}{S}}}-\text{C}_6H_4-NH_2$ |
| H | $-\overset{O}{\underset{\|}{C}}-CH_3$ |
| H | $-\overset{O}{\underset{\|}{C}}-C_2H_5$ |
| H | $-\overset{O}{\underset{\|}{C}}-(CH_2)_2CH_3$ |
| H | $-\overset{O}{\underset{\|}{C}}-(CH_2)_3CH_3$ |

EXAMPLE 28

Following the procedure of Example 1 but substituting for the ethoxymethylene malonic acid diethyl ester in part (a) the malonic acid esters of column I the compounds listed in column II are obtained:

| Column I | Column II |
|---|---|
| $C_2H_5-O-\underset{\underset{C-C_2H_5}{\|}}{\overset{CH_3}{C=C}}\overset{O}{\underset{\|}{C}}-C_2H_5$ | 4-chloro-1-ethyl-6-methyl-1H-pyrazolo[3,4-b]pyridine-5-methanol |
| $C_2H_5-O-\underset{\underset{C-C_2H_5}{\|}}{\overset{C_2H_5}{C=C}}\overset{O}{\underset{\|}{C}}-C_2H_5$ | 4-chloro-1,6-diethyl-1H-pyrazolo[3,4-b]pyridine-5-methanol |

| Column I | Column II |
|---|---|
| $C_2H_5-O-\underset{\underset{C-C_2H_5}{\|}}{\overset{C_3H_7}{C=C}}\overset{O}{\underset{\|}{C}}-C_2H_5$ | 4-chloro-1-ethyl-6-propyl-1H-pyrazolo[3,4-b]pyridiene-5-methanol |
| $C_2H_5-O-\underset{\underset{C-C_2H_5}{\|}}{\overset{C_4H_9}{C=C}}\overset{O}{\underset{\|}{C}}-C_2H_5$ | 4-chloro-1-ethyl-6-butyl-1H-pyrazolo[3,4-b]pyridine-5-methanol |
| $C_2H_5-O-\underset{\underset{C-C_2H_5}{\|}}{\overset{C_6H_5}{C=C}}\overset{O}{\underset{\|}{C}}-C_2H_5$ | 4-chloro-1-ethyl-6-phenyl-1H-pyrazolo[3,4-b]pyridine-5-methanol |

EXAMPLE 29

Following the procedure of Example 1 but omitting part (c), the 1-ethyl-4-hydroxy-1H-pyrazolo[3,4-b]pyridine-5-methanol is obtained.

EXAMPLE 30

Following the procedure of Example 3 but substituting for the ethyl iodide in part (a) iodobenzene and benzyliodide, 1-ethyl-4-phenoxy-1H-pyrazolo[3,4-b]pyridine-5-methanol and 1-ethyl-4-benzyloxy-1H-pyrazolo[3,4-b]pyridine-5-methanol, respectively, are obtained.

What is claimed is:

1. A compound of the formula:

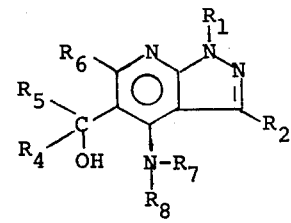

wherein $R_1$ is selected from the group consisting of hydrogen, lower alkyl, phenyl, phenyl-lower alkyl, and cycloalkyl of 3 to 7 carbon atoms; and $R_2$ is selected from the group consisting of hydrogen, lower alkyl, and phenyl; $R_7$ and $R_8$ are each independently selected from the group consisting of hydrogen, lower alkyl, lower alkenyl, cycloalkyl of 3 to 7 carbon atoms,

phenyl, phenyl-lower alkyl

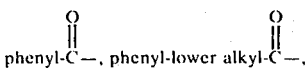

di-lower alkylamino-lower alkyl, lower alkyl-sulfonyl, phenyl-sulfonyl, and mono and disubstituted phenyl, phenyl-lower alkyl,

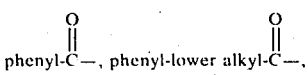

and phenyl-sulfonyl wherein said phenyl substituents are selected from the group consisting of halogen, lower alkyl, trifluoromethyl, amino and carboxy; and $R_4$ and $R_5$ are independently selected from the group consisting of hydrogen, lower alkyl, phenyl, mono and disubstituted phenyl wherein said phenyl substituents are as set forth above, phenyl-lower alkyl, and cycloalkyl of 3 to 7 carbon atoms; and $R_6$ is selected from the group consisting of hydrogen, lower alkyl, and phenyl; and their pharmaceutically acceptable salts.

2. A compound as in claim 1 wherein $R_7$ and $R_8$ are independently selected from the group consisting of hydrogen, lower alkyl of 1 to 4 carbons, lower alkenyl of 2 to 4 carbons, cycloalkyl of 5 to 6 carbons,

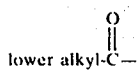

wherein lower alkyl is of 1 to 4 carbons, di-lower alkylamino-lower alkyl wherein each lower alkyl is of 1 to 4 carbons, phenyl, benzyl, phenethyl, benzoyl,

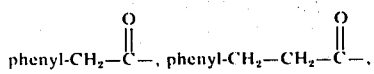

phenyl-sulfonyl, lower alkyl-sulfonyl of 1 to 4 carbons, and mono and disubstituted phenyl, benzyl, phenethyl, benzoyl,

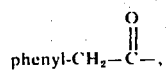

and phenyl-sulfonyl wherein said substituents are selected from the group consisting of halogen, lower alkyl of 1 to 4 carbons, $CF_3$, amino and carboxy.

3. A compound as in claim 2 wherein $R_1$ is selected from the group consisting of hydrogen, lower alkyl of 1 to 4 carbons, phenyl, benzyl, phenethyl, and cycloalkyl of 5 to 6 carbons; and $R_2$ is selected from the group consisting of hydrogen, lower alkyl of 1 to 4 carbon atoms, and phenyl; and $R_4$ and $R_5$ are each independently selected from the group consisting of hydrogen, lower alkyl of 1 to 4 carbons, phenyl, benzyl, phenethyl, cycloalkyl of 5 to 6 carbons, and mono and disubstituted phenyl wherein said substituents are selected from the group consisting of halogen, lower alkyl of 1 to 4 carbons, $CF_3$, amino and carboxy; and $R_6$ is selected from the group consisting of hydrogen, lower alkyl of 1 to 4 carbons, and phenyl.

4. A compound as in claim 3 wherein $R_1$, $R_2$, and $R_6$ are each independently selected from the group consisting of hydrogen, and lower alkyl of 1 to 4 carbons; and $R_4$ and $R_5$ are independently selected from the group consisting of hydrogen, lower alkyl of 1 to 4 carbons, and phenyl; and $R_7$ and $R_8$ are independently selected from the group consisting of hydrogen and lower alkyl of 1 to 4 carbons.

5. A compound as in claim 4 wherein $R_1$ is selected from the group consisting of hydrogen and ethyl; and $R_2$ and $R_6$ are independently selected from the group consisting of hydrogen and methyl; and $R_4$ and $R_5$ are independently selected from the group consisting of hydrogen, ethyl, butyl and phenyl; and $R_7$ and $R_8$ are independently selected from the group consisting of hydrogen and butyl.

6. A compound as in claim 5 having the name 4-buylamino-1-ethyl-1H-pyrazolo[3,4-b]pyridine-5-methanol.

7. A compound as in claim 5 having the name 4-butylamino-1-ethyl-3-methyl-1H-pyrazolo[3,4-b]-pyridine-5-methanol.

8. A compound as in claim 5 having the name 4-butylamino-1-ethyl-1H-pyrazolo[3,4-b]pyridine-5-diethyl carbinol.

9. A compound as in claim 5 having the name 4-butylamino-1-ethyl-1H-pyrazolo[3,4-b]pyridine-5-dibutyl carbinol.

10. A compound as in claim 5 having the name 4-amino-1H-pyrazolo[3,4-b]pyridine-5-phenyl carbinol.

11. A compound as in claim 5 having the name 4-butylamino-1-ethyl-1H-pyrazolo[3,4-b]pyridine-5-diphenyl carbinol.

* * * * *

UNITED STATES PATENT OFFICE
CERTIFICATE OF CORRECTION

Patent No. 3,983,128    Dated September 28, 1976

Inventor(s)    Hans Hoehn et al.

It is certified that error appears in the above-identified patent and that said Letters Patent are hereby corrected as shown below:

Column 2, line 36, "cyclohepty" should read -- cycloheptyl --.

Column 11, line 35, "Examples" should read -- Example --.

Column 11, line 39, "and" should read -- an --.

Column 11, line 46, "evaported" should read -- evaporated --.

Column 13, line 1, "[3,4]" should read -- [3,4-b] --.

Signed and Sealed this

Twenty-fifth Day of January 1977

[SEAL]

Attest:

RUTH C. MASON
*Attesting Officer*

C. MARSHALL DANN
*Commissioner of Patents and Trademarks*